(12) United States Patent
Jo et al.

(10) Patent No.: US 9,440,090 B2
(45) Date of Patent: Sep. 13, 2016

(54) PHOTO-THERAPY METHOD USING A DISPLAY DEVICE

(71) Applicant: Samsung Display Co., LTD., Yongin, Gyeonggi-Do (KR)

(72) Inventors: Min-Gyeong Jo, Busan (KR); Jong-In Baek, Suwon-si (KR); Won-Sang Park, Yongin-si (KR); Jong-Ho Hong, Seongnam-si (KR)

(73) Assignee: Samsung Display Co., LTD. (KR)

( * ) Notice: Subject to any disclaimer, the term of this patent is extended or adjusted under 35 U.S.C. 154(b) by 223 days.

(21) Appl. No.: 14/165,196

(22) Filed: Jan. 27, 2014

(65) Prior Publication Data
US 2015/0051672 A1 Feb. 19, 2015

(30) Foreign Application Priority Data
Aug. 19, 2013 (KR) ........................ 10-2013-0097894

(51) Int. Cl.
*A61N 5/06* (2006.01)

(52) U.S. Cl.
CPC ......... *A61N 5/06* (2013.01); *A61N 2005/0626* (2013.01)

(58) Field of Classification Search
CPC .................................................... A61N 5/06
USPC ............. 607/77–95; 345/612–614, 694–696, 345/698, 690, 211–212
See application file for complete search history.

(56) References Cited

U.S. PATENT DOCUMENTS

| 8,200,340 B2 | 6/2012 | Skelton et al. | |
| 2003/0080931 A1* | 5/2003 | Chen .................... | G09G 3/2011 345/88 |
| 2003/0103058 A1* | 6/2003 | Hellen Brown Elliott ....................... | G09G 3/20 345/589 |
| 2004/0189679 A1* | 9/2004 | Ito ........................... | G09G 3/20 345/690 |
| 2007/0078652 A1* | 4/2007 | Chang .................... | G10L 15/00 704/234 |
| 2008/0214944 A1 | 9/2008 | Morris et al. | |
| 2011/0184498 A1* | 7/2011 | Donley ................ | A61B 3/0041 607/88 |
| 2012/0295376 A1 | 11/2012 | Lee et al. | |

FOREIGN PATENT DOCUMENTS

| KR | 2011-0092630 | 8/2011 |
| KR | 2012-0052754 | 5/2012 |
| KR | 2013-0026294 | 3/2013 |

OTHER PUBLICATIONS

Home Therapy Solutions, http://www.visiontherapysolutions.net/co.php#1, accessed Apr. 5, 2012.*

* cited by examiner

*Primary Examiner* — Lynsey Crandall
*Assistant Examiner* — Dacheng Xie
(74) *Attorney, Agent, or Firm* — Innovation Counsel LLP (57) ABSTRACT

A photo-therapy method using a display device is provided. The photo-therapy method includes receiving a viewing time input and a photo-therapy selection input, wherein the viewing time input represents an expected viewing time of a user and the photo-therapy selection input represents a photo-therapy selected by the user. The photo-therapy method further includes calculating a period of a photo-therapy image based on the expected viewing time and a suggested treatment time of the selected photo-therapy, and displaying the photo-therapy image with the calculated period while displaying a normal image.

17 Claims, 8 Drawing Sheets

PHOTO-THERAPY METHOD USING A DISPLAY DEVICE

CROSS REFERENCE TO RELATED APPLICATION

This application claims priority under 35 U.S.C. §119 to Korean Patent Application No. 10-2013-0097894 filed on Aug. 19, 2013, the disclosure of which is herein incorporated by reference in its entirety.

BACKGROUND

1. Technical Field

The present disclosure generally relates to display devices. More particularly, the present disclosure relates to photo-therapy methods using the display devices, and display devices capable of performing the photo-therapy methods.

2. Description of the Related Art

Recently, photo-therapy devices that radiate light to a human body have been developed. The photo-therapy devices can be used to improve skin care, control biorhythm, treat depression, etc. However, current photo-therapy devices are typically configured for a particular type of treatment (such as anti-inflammatory therapy, pimple therapy, wrinkle therapy, skin lightening therapy, biorhythm control, or depression therapy). As a result, a user may require different photo-therapy devices for different treatments. Furthermore, the current photo-therapy devices may not be able to display other images (such as visual images) while the user is undergoing photo-therapy.

SUMMARY

The present disclosure is directed to address at least the above deficiencies in current photo-therapy devices.

According to some embodiments of the inventive concept, a photo-therapy method using a display device is provided. The photo-therapy method includes receiving a viewing time input and a photo-therapy selection input, wherein the viewing time input represents an expected viewing time of a user and the photo-therapy selection input represents a photo-therapy selected by the user; calculating a period of a photo-therapy image based on the expected viewing time and a suggested treatment time of the selected photo-therapy; and displaying the photo-therapy image with the calculated period while displaying a normal image.

In some embodiments, the photo-therapy image may be distributed uniformly temporally during the expected viewing time.

In some embodiments, the period of the photo-therapy image may be proportional to the expected viewing time, and may be inversely proportional to the suggested treatment time.

In some embodiments, the period of the photo-therapy image may be longer than a period that is perceptible by the user.

In some embodiments, the expected viewing time may be longer than a minimum viewing time, such that a number of frames per second of the photo-therapy image is less than a number of frames per second that is perceptible by the user.

In some embodiments, the photo-therapy method may further include informing the user that the expected viewing time is shorter than the minimum viewing time when a first viewing time input is received, wherein the first viewing time input indicates the expected viewing time is shorter than the minimum viewing time; and further receiving a second viewing time input from the user.

In some embodiments, displaying the photo-therapy image may include displaying a synthesized image by synthesizing the photo-therapy image and the normal image with the calculated period.

In some embodiments, the synthesized image may be generated by adding a predetermined value to at least one sub-pixel data, wherein the at least one sub-pixel data may be selected from among red sub-pixel data, green sub-pixel data, and blue sub-pixel data of the normal image based on the selected photo-therapy.

In some embodiments, the synthesized image may be generated by multiplying a predetermined value with at least one sub-pixel data, wherein the at least one sub-pixel data may be selected from among red sub-pixel data, green sub-pixel data, and blue sub-pixel data of the normal image based on the selected photo-therapy.

In some embodiments, the synthesized image may be generated by converting at least one sub-pixel data to a maximum sub-pixel data, wherein the at least one sub-pixel data may be selected from among red sub-pixel data, green sub-pixel data, and blue sub-pixel data of the normal image based on the selected photo-therapy.

In some embodiments, displaying the photo-therapy image may include displaying the photo-therapy image by inserting the photo-therapy image between normal images with the calculated period.

In some embodiments, displaying the photo-therapy image may include displaying a synthesized image by synthesizing the photo-therapy image into a portion of the normal image with the calculated period.

In some embodiments, a position of the portion of the normal image into which the photo-therapy image is synthesized may be randomly determined each time the synthesized image is displayed.

According to some other embodiments of the inventive concept, a display device is provided. The display device includes a display panel; an input unit configured to receive a viewing time input and a photo-therapy selection input, wherein the viewing time input represents an expected viewing time of a user and the photo-therapy selection input represents a photo-therapy selected by the user; and a display controller configured to calculate a period of a photo-therapy image based on the expected viewing time and a suggested treatment time of the selected photo-therapy, and to control the display panel to display the photo-therapy image with the calculated period while displaying a normal image.

In some embodiments, the photo-therapy image may be distributed uniformly temporally during the expected viewing time.

In some embodiments, the period of the photo-therapy image may be proportional to the expected viewing time, and may be inversely proportional to the suggested treatment time.

In some embodiments, the period of the photo-therapy image may be longer than a period that is perceptible by the user.

In some embodiments, the display controller may control the display panel to display a synthesized image by synthesizing the photo-therapy image and the normal image with the calculated period.

In some embodiments, the display controller may control the display panel to display the photo-therapy image by inserting the photo-therapy image between normal images with the calculated period.

In some embodiments, the display controller may control the display panel to display a synthesized image by synthesizing the photo-therapy image into a portion of the normal image with the calculated period.

DETAILED DESCRIPTION

The exemplary embodiments will be described more fully herein with reference to the accompanying drawings. The inventive concept may be embodied in different forms and should not be construed as being limited to the described embodiments. In the drawings, the sizes and relative sizes of the layers and regions may be exaggerated for clarity.

It will be understood that when an element or layer is referred to as being "on", "connected to", or "coupled to" another element or layer, it can be directly on, connected or coupled to the other element or layer, or with one or more intervening elements or layers being present. In contrast, when an element is referred to as being "directly on", "directly connected to", or "directly coupled to" another element or layer, there are no intervening elements or layers present. Like or similar reference numerals refer to like or similar elements throughout. As used herein, the term "and/or" includes any and all combinations of one or more of the associated listed items.

It will be understood that, although the terms "first", "second", "third", etc. may be used herein to describe various elements, components, regions, layers, patterns and/or sections, the elements, components, regions, layers, patterns and/or sections should not be limited by those terms. Those terms are only used to distinguish an element, component, region, layer pattern or section from another region, layer, pattern or section. Thus, a "first" element, component, region, layer or section could be easily termed a "second" element, component, region, layer or section without departing from the teachings of inventive concept.

Spatially relative terms, such as "beneath", "below", "lower", "above", "upper", and the like, may be used to describe the relationship of an element or feature to another element(s) or feature(s) as illustrated in the figures. It will be understood that the spatially relative terms are intended to encompass different orientations of the device in addition to the orientation depicted in the figures. For example, if the device in the figures is turned over, elements described as "below" or "beneath" other elements or features would then be oriented "above" the other elements or features. Thus, the term "below" can encompass both an orientation of "above" and "below". Also, the device may be oriented (rotated 90 degrees or at other orientations) and the spatially relative descriptors used herein may be interpreted accordingly.

The terminology used herein is for describing the embodiments and is not intended to limit the inventive concept. As used herein, the singular forms "a", "an", and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

The exemplary embodiments described herein with reference to cross sectional illustrations are schematic illustrations of idealized embodiments (and/or intermediate structures) of the inventive concept. As such, variations from the shapes of the illustrations as a result of, for example, manufacturing techniques and/or tolerances, are to be expected. Thus, the embodiments should not be construed as being limited to the particular shapes of regions illustrated herein but also include deviations in shapes that result, for example, from manufacturing. The regions illustrated in the figures are schematic in nature and their shapes are not intended to illustrate the actual shape of a region of a device and are not intended to limit the scope of the inventive concept.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art, and should not be interpreted in an idealized or overly formal sense unless expressly defined herein.

Figure 1:
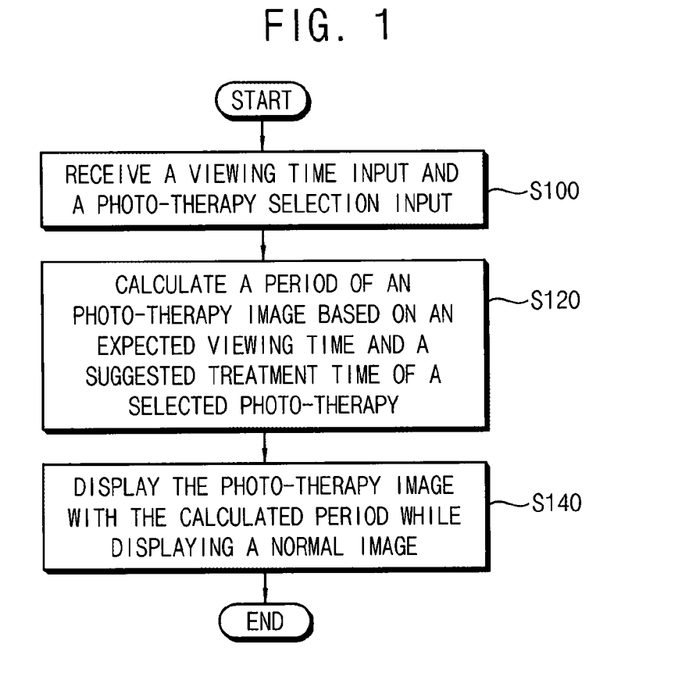
FIG. 1 is a flowchart illustrating a photo-therapy method using a display device in accordance with an exemplary embodiment.

FIG. 1 is a flowchart illustrating a photo-therapy method using a display device in accordance with an exemplary embodiment.

Referring to FIG. 1, the display device first receives a viewing time input and a photo-therapy selection input (S100). The display device may receive the viewing time input (representing an expected viewing time) from a user using an input unit. The display device may further receive the photo-therapy selection input (representing a type of photo-therapy selected by the user using the input unit). For example, the photo-therapy selected by the user may include at least one of the following therapies: anti-inflammatory therapy, pimple therapy, wrinkle therapy, skin lightening therapy, biorhythm control, depression therapy, etc. In some embodiments, the display device may store in a storing unit the type of photo-therapy previously selected by the user, and receive from the storing unit a photo-therapy selection input (representing the previously selected photo-therapy) when the viewing time input is received.

Next, the display device calculates a period of a photo-therapy image based on the expected viewing time (from the viewing time input) and a suggested treatment time of the selected photo-therapy (from the photo-therapy selection input) (S120). The period of the photo-therapy image is proportional to the expected viewing time and inversely proportional to the suggested treatment time. The suggested treatment time may be predetermined according to the type of photo-therapy. For example, if the selected photo-therapy is an anti-inflammatory therapy, pimple therapy, or wrinkle therapy, the suggested treatment time may range from about 2 minutes to about 3 minutes. If the selected photo-therapy is a biorhythm control or depression therapy, the suggested treatment time may take longer than about 10 minutes.

When the expected viewing time is increased, the display device may determine a longer period for the photo-therapy image, and may decrease the number of frames per second (fps) of the photo-therapy image. When the suggested treatment time is increased, the display device may determine a shorter period for the photo-therapy image, and may increase the number of frames per second (fps) of the photo-therapy image. In some embodiments, the display device may determine the period of the photo-therapy image such that the photo-therapy image is distributed uniformly (temporally) during the expected viewing time.

In some embodiments, the display device may determine the period of the photo-therapy image such that the period of the photo-therapy image is longer than a period that is perceptible by the user. For example, when the period of the photo-therapy image is shorter than about 1 second, the photo-therapy image may be perceptible by the user. Thus, the period of the photo-therapy image may be set to be equal to or longer than about 1 second. The display device may set the expected viewing time to be longer than a minimum viewing time, such that the number of frames per second of the photo-therapy image is less than the number of frames per second that is perceptible by the user. For example, when the number of frames per second of the photo-therapy image is greater than about 1 frame per second, the photo-therapy image may be perceptible by the user. Thus, the photo-therapy image may be displayed at about 1 frame per second (fps or Hz) or less while respective images (including the photo-therapy image and a normal image) may be displayed at a predetermined frequency (e.g., 60 Hz, 120 Hz, 240 Hz, or the like). This ensures that the period of the photo-therapy image is longer than the period that is perceptible by the user, and that the number of frames per second of the photo-therapy image is less than the number of frames per second that is perceptible by the user. Accordingly, the photo-therapy may be provided to the user without the user noticing (or perceiving) the photo-therapy image. In some embodiments, when the display device receives the viewing time input indicating that the expected viewing time is shorter than the minimum viewing time, the display device may inform the user that the expected viewing time is shorter than the minimum viewing time, and may further receive another viewing time input from the user.

Next, the display device displays the photo-therapy image with the calculated period while displaying a normal image (S140). Here, the normal image may be an image displayed by the display device for its original purpose other than photo-therapy. For example, if the display device is a television, the normal image may be a television program image. If the display device is a smart phone, the normal image may be a video being played on the smart phone or a game image.

The photo-therapy image may include high intensity light at a predetermined wavelength for the selected photo-therapy. For example, if the selected photo-therapy is an anti-inflammatory therapy or pimple therapy, the photo-therapy image may include high intensity light at a wavelength of about 660 nm. If the selected photo-therapy is a wrinkle therapy, the photo-therapy image may include high intensity light at a wavelength ranging from about 630 nm to about 660 nm. If the selected photo-therapy is a skin lightening therapy, the photo-therapy image may include high intensity light at a wavelength of about 525 nm. If the selected photo-therapy is a biorhythm control or depression therapy, the photo-therapy image may include high intensity light at a wavelength ranging from about 446 nm to about 477 nm.

In some embodiments, to display the photo-therapy image with the calculated period while displaying the normal image, the display device may synthesize the photo-therapy image and the normal image with the calculated period, so as to display a synthesized image. In other embodiments, the display device may display the photo-therapy image by inserting the photo-therapy image between the normal images with the calculated period.

In some other embodiments, the display device may synthesize the photo-therapy image into a portion of the normal image with the calculated period, so as to display a synthesized image. In those other embodiments, a position of the portion of the normal image (into which the photo-therapy image is synthesized) may be randomly determined each time the synthesized image is displayed.

As described above, the photo-therapy method using the display device according to the embodiment of FIG. 1 allows the photo-therapy image with the calculated period to be displayed while displaying the normal image. Accordingly, the user may undergo the photo-therapy while watching the normal image. Furthermore, the exemplary display device may determine the period of the photo-therapy image to be longer than the period that is perceptible by the user. Accordingly, the user may undergo the photo-therapy without noticing (or perceiving) the photo-therapy image. In addition, in some embodiments, the exemplary photo-therapy method may allow various photo-therapies to be provided to a user using a single display device.

Figure 2:
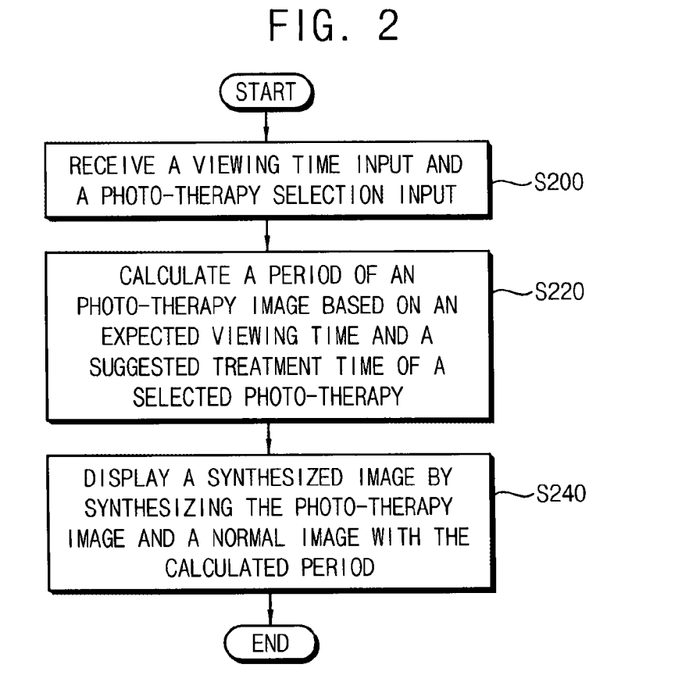
FIG. 2 is a flowchart illustrating a photo-therapy method using a display device in accordance with another exemplary embodiment.
Figure 3:
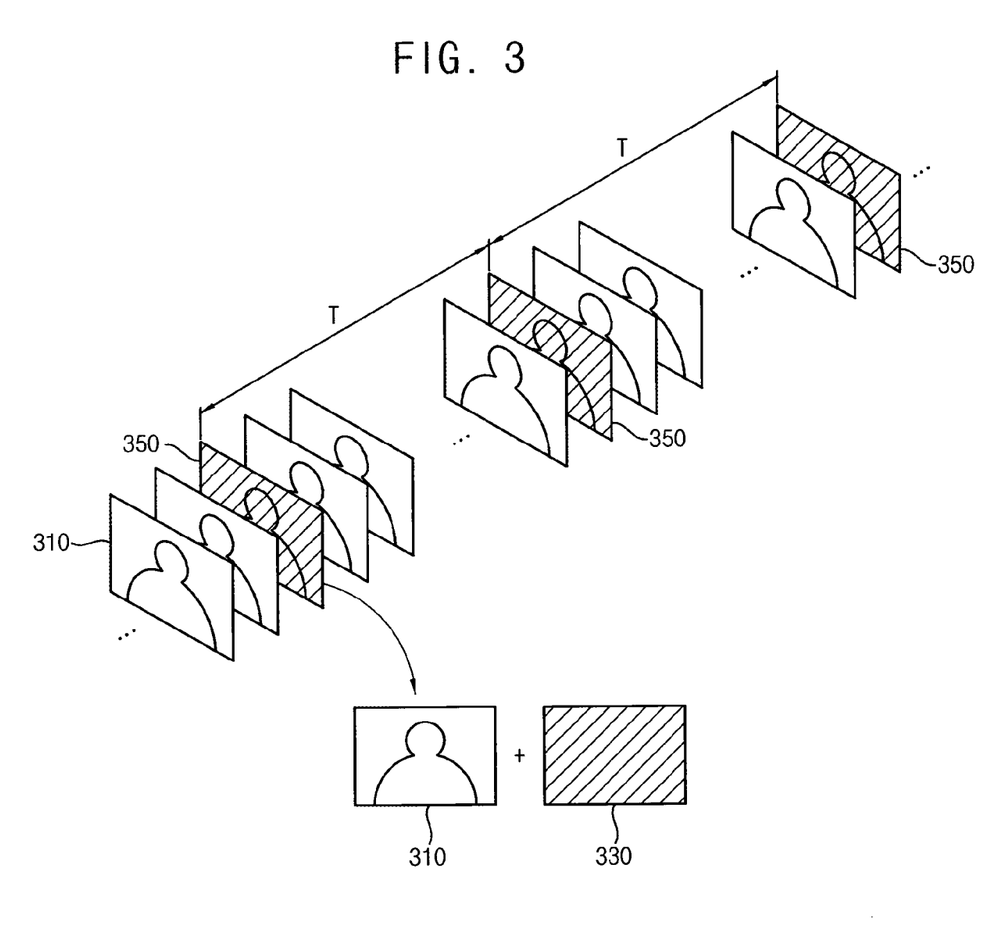
FIG. 3 is a diagram illustrating image frames displayed using the photo-therapy method of FIG. 2.
Figure 4A:
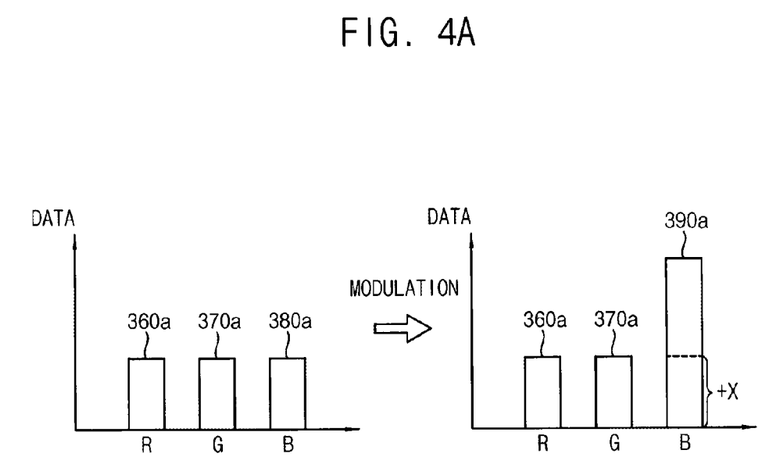
FIGS. 4A through 4C are diagrams describing exemplary processes for synthesizing the photo-therapy images and normal images and displaying the synthesized image using the photo-therapy method of FIG. 2.
Figure 4B:
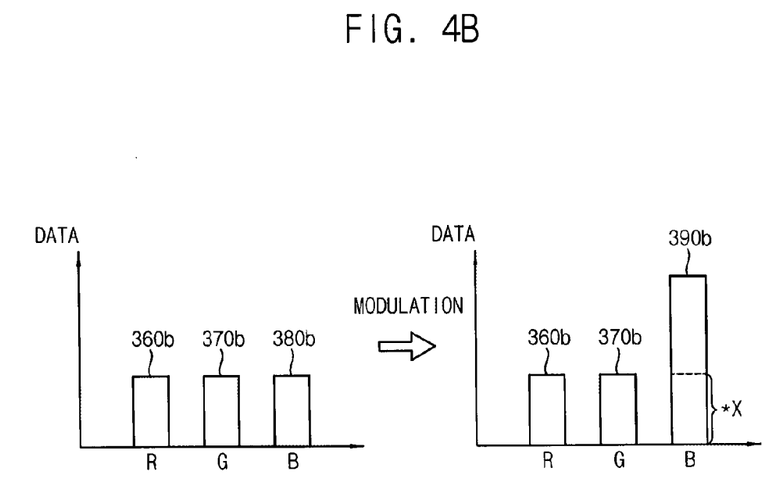
Figure 4C:
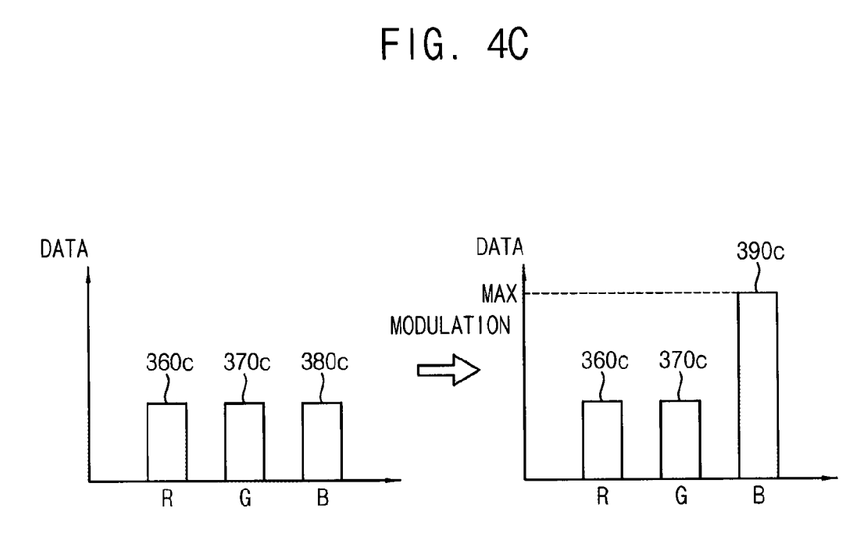

FIG. 2 is a flowchart illustrating a photo-therapy method using a display device in accordance with another exemplary embodiment. FIG. 3 is a diagram illustrating image frames displayed using the photo-therapy method of FIG. 2. FIGS. 4A through 4C are diagrams describing exemplary processes for synthesizing the photo-therapy images and normal images and displaying the synthesized image using the photo-therapy method of FIG. 2.

Referring to FIG. 2, the display device first receives a viewing time input (representing an expected viewing time of a user) and a photo-therapy selection input (representing a photo-therapy selected by the user) (S200). The display device then calculates a period of a photo-therapy image based on the expected viewing time and a suggested treatment time of the selected photo-therapy (S220). In some embodiments, the display device may determine the period of the photo-therapy image such that the photo-therapy image is distributed uniformly (temporally) during the expected viewing time. In some embodiments, the display device may set the expected viewing time to be longer than a minimum viewing time, such that the number of frames per second of the photo-therapy image is less than the number of frames per second that is perceptible by the user. Accordingly, the user may undergo the photo-therapy without noticing (or perceiving) the photo-therapy image.

To display the photo-therapy image along with a normal image, the display device may synthesize the photo-therapy image and the normal image with the calculated period so as to display a synthesized image (S240). For example, as illustrated in FIG. 3, the display image may display a normal image 310 for an original purpose of the display device, and may display a synthesized image 350 by synthesizing a photo-therapy image 330 and the normal image 310 with the period T. The period T is calculated based on the expected viewing time and the suggested treatment time.

In some embodiments (see FIG. 4A), the display device may add a predetermined value X to at least one sub-pixel data. The sub-pixel data is selected from among red sub-pixel data 360*a*, green sub-pixel data 370*a*, and blue sub-pixel data 380*a* of the normal image for each pixel based on the selected photo-therapy. After adding the predetermined value X to the selected sub-pixel data, the display device may then generate a synthesized image including an amplified sub-pixel data 390*a*. In the example of FIG. 4A, the display device adds a predetermined value X to the blue sub-pixel data 380*a* and then generates a synthesized image including an amplified sub-pixel data 390*a*.

As previously described with reference to FIG. 4A, the sub-pixel data is selected from among the red sub-pixel data 360*a*, green sub-pixel data 370*a*, and blue sub-pixel data 380*a* of the normal image for each pixel based on the selected photo-therapy. For example, if the selected photo-therapy is an anti-inflammatory therapy, pimple therapy or wrinkle therapy, the display device may add the predetermined value X to the red sub-pixel data 360*a* to generate the synthesized image. If the selected photo-therapy is a skin lightening therapy, the display device may add the predetermined value X to the green sub-pixel data 370*a* to generate the synthesized image. If the selected photo-therapy is a biorhythm control or depression therapy, the display device may add the predetermined value X to the blue sub-pixel data 380*a* to generate the synthesized image.

In some other embodiments (see FIG. 4B), the display device may multiply a predetermined value X with at least one sub-pixel data. The sub-pixel data is selected from among red sub-pixel data 360*b*, green sub-pixel data 370*b*, and blue sub-pixel data 380*b* of the normal image for each pixel based on the selected photo-therapy. After multiplying the predetermined value X with the selected sub-pixel data, the display device may then generate a synthesized image including an amplified sub-pixel data 390*b*. In the example of FIG. 4B, the display device multiplies a predetermined value X with the blue sub-pixel data 380*b* and then generates a synthesized image including an amplified sub-pixel data 390*b*.

As previously described with reference to FIG. 4B, the sub-pixel data is selected from among the red sub-pixel data 360*b*, green sub-pixel data 370*b*, and blue sub-pixel data 380*b* of the normal image for each pixel based on the selected photo-therapy. For example, if the selected photo-therapy is an anti-inflammatory therapy, pimple therapy or wrinkle therapy, the display device may multiply the predetermined value X with the red sub-pixel data 360*b* to generate the synthesized image. If the selected photo-therapy is a skin lightening therapy, the display device may multiply the predetermined value X with the green sub-pixel data 370*b* to generate the synthesized image. If the selected photo-therapy is a biorhythm control or depression therapy, the display device may multiply the predetermined value X with the blue sub-pixel data 380*b* to generate the synthesized image.

In some further embodiments (see FIG. 4C), the display device may convert at least one sub-pixel data into a maximum sub-pixel data 390*c*. The sub-pixel data is selected from among red sub-pixel data 360*c*, green sub-pixel data 370*c*, and blue sub-pixel data 380*c* of the normal image for each pixel based on the selected photo-therapy. After converting the selected sub-pixel data into the maximum sub-pixel data 390*c*, the display device may then generate a synthesized image including the maximum sub-pixel data 390*c*. In the example of FIG. 4C, the display device converts the blue sub-pixel data 380*c* into a maximum sub-pixel data 390*c* and then generates a synthesized image including the maximum sub-pixel data 390*c*.

As previously described with reference to FIG. 4C, the sub-pixel data is selected from among red sub-pixel data 360*c*, green sub-pixel data 370*c*, and blue sub-pixel data 380*c* of the normal image for each pixel based on the selected photo-therapy. For example, if the selected photo-therapy is an anti-inflammatory therapy, pimple therapy, or wrinkle therapy, the display device may convert the red sub-pixel data 360*c* into a maximum sub-pixel data 390*c* to generate the synthesized image. If the selected photo-therapy is a skin lightening therapy, the display device may convert the green sub-pixel data 370*c* into a maximum sub-pixel data 390*c* to generate the synthesized image. If the selected photo-therapy is a biorhythm control or depression therapy, the display device may convert the blue sub-pixel data 380*c* into a maximum sub-pixel data 390*c* to generate the synthesized image.

As described above, the photo-therapy method using the display device according to the different embodiments in FIGS. 2, 3, and 4A-C allows the synthesized image to be displayed while displaying the normal image. The synthesized image can be obtained by synthesizing the photo-therapy image and the normal image with the period (the period being calculated based on the expected viewing time and the suggested treatment time). Accordingly, the user may undergo the photo-therapy while watching the normal image. Furthermore, the exemplary display device may determine the period of the photo-therapy image to be longer than the period that is perceptible by the user. Accordingly, the user may undergo the photo-therapy without noticing (or perceiving) the photo-therapy image. In addition, in some embodiments, the exemplary photo-therapy method may allow various photo-therapies to be provided to a user using a single display device.

Figure 5:
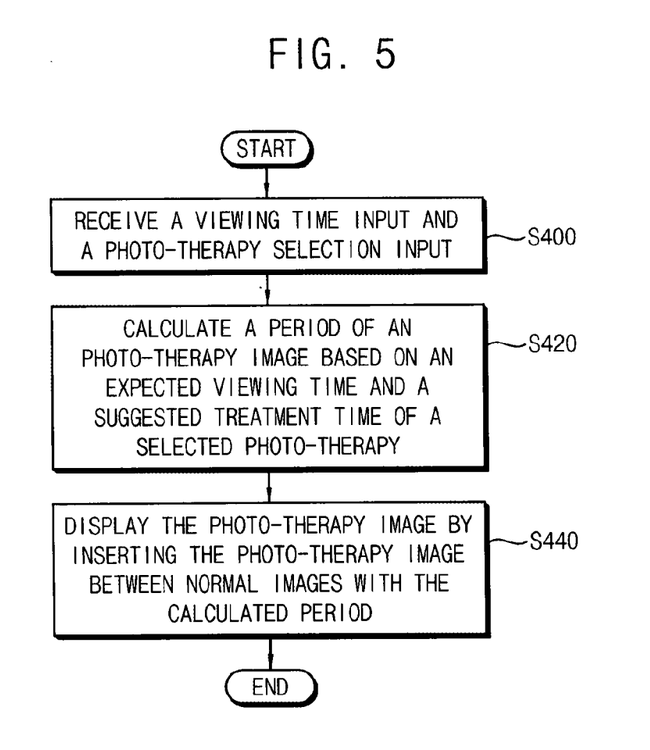
FIG. 5 is a flowchart illustrating a photo-therapy method using a display device in accordance with a further exemplary embodiment.
Figure 6:
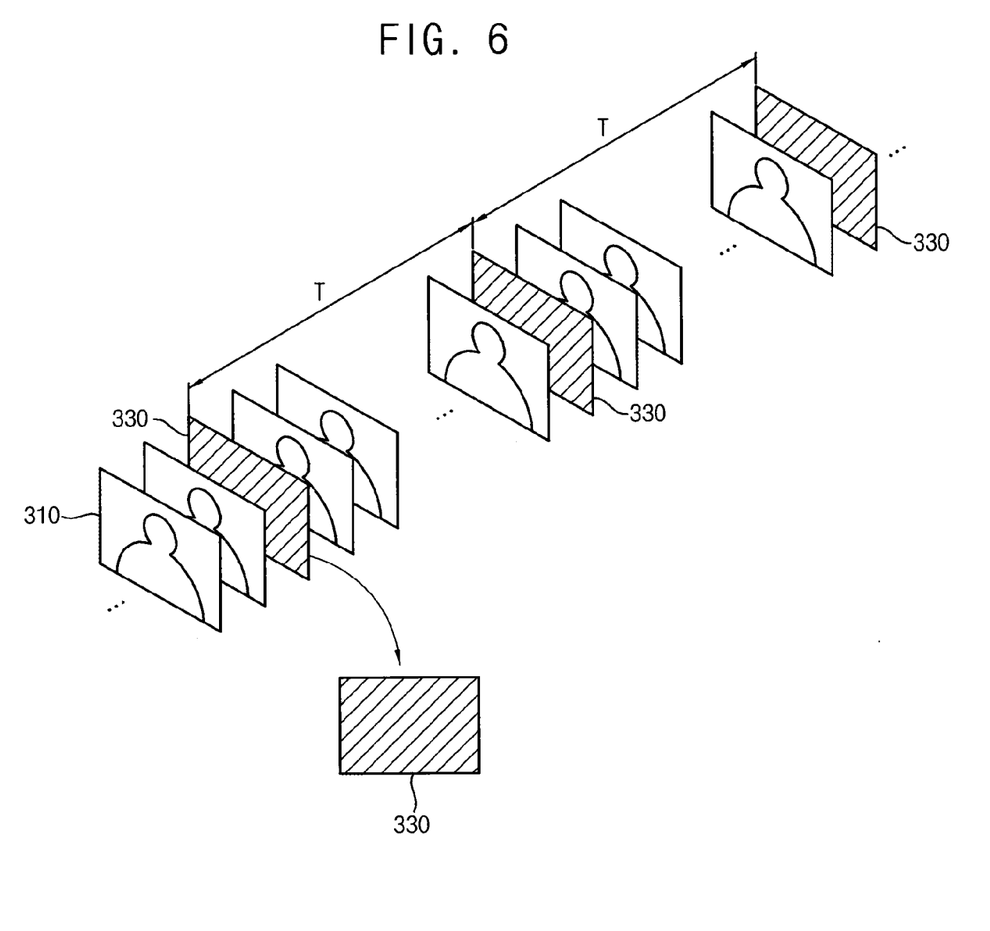
FIG. 6 is a diagram illustrating image frames displayed using the photo-therapy method of FIG. 5.

FIG. 5 is a flowchart illustrating a photo-therapy method using a display device in accordance with a further exemplary embodiment. FIG. 6 is a diagram illustrating image frames displayed using the photo-therapy method of FIG. 5.

Referring to FIG. 5, a display device first receives a viewing time input (representing an expected viewing time of a user) and a photo-therapy selection input (representing a photo-therapy selected by the user) (S400). The display device then calculates a period of a photo-therapy image based on the expected viewing time and a suggested treatment time of the selected photo-therapy (S420). In some embodiments, the display device may determine the period of the photo-therapy image such that the photo-therapy image is distributed uniformly (temporally) during the expected viewing time. In some embodiments, the display device may set the expected viewing time to be longer than a minimum viewing time, such that the number of frames per second of the photo-therapy image is less than the number of frames per second that is perceptible by the user. Accordingly, the user may undergo the photo-therapy without noticing (or perceiving) the photo-therapy image.

Next, the display device may display the photo-therapy image by inserting the photo-therapy image between normal images with the calculated period (S440). For example, as illustrated in FIG. 6, the display image may display normal images 310 for an original purpose of the display device, and display a photo-therapy image 330 by inserting the photo-therapy image 330 between the normal images 310 with the period T. The period T is calculated based on the expected viewing time and the suggested treatment time.

As described above, the photo-therapy method using the display device according to the embodiment of FIGS. 5 and 6 allows the photo-therapy image to be displayed while displaying the normal images. The photo-therapy image is displayed by inserting the photo-therapy image between the normal images with the period (the period being calculated based on the expected viewing time and the suggested treatment time). Accordingly, the user may undergo the photo-therapy while watching the normal image. Furthermore, the exemplary display device may determine the period of the photo-therapy image to be longer than the period that is perceptible by the user. Accordingly, the user may undergo the photo-therapy without noticing (or perceiving) the photo-therapy image. In addition, in some embodiments, the exemplary photo-therapy method may allow various photo-therapies to be provided to a user using a single display device.

Figure 7:
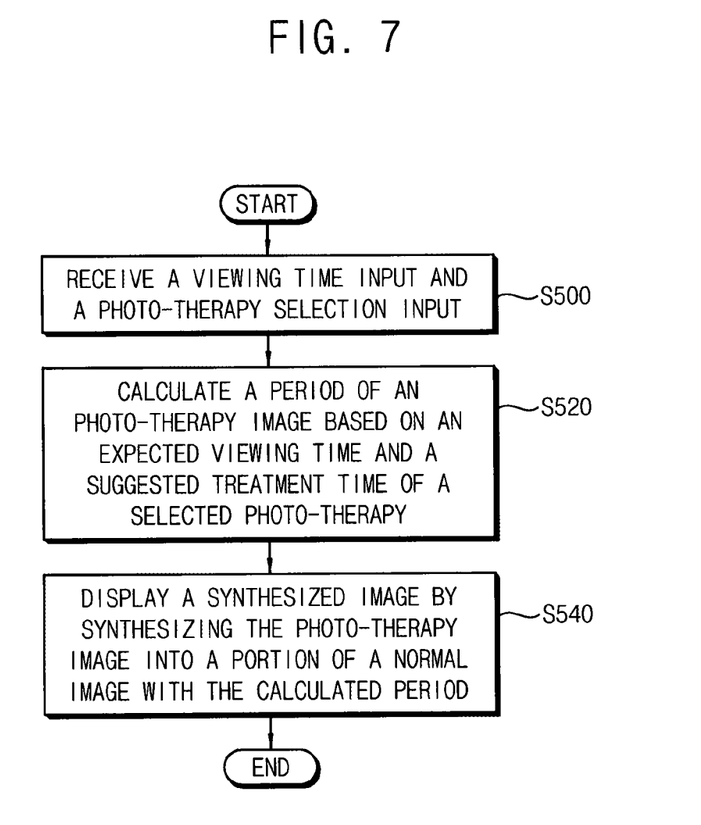
FIG. 7 is a flowchart illustrating a photo-therapy method using a display device in accordance with another further exemplary embodiment.
Figure 8:
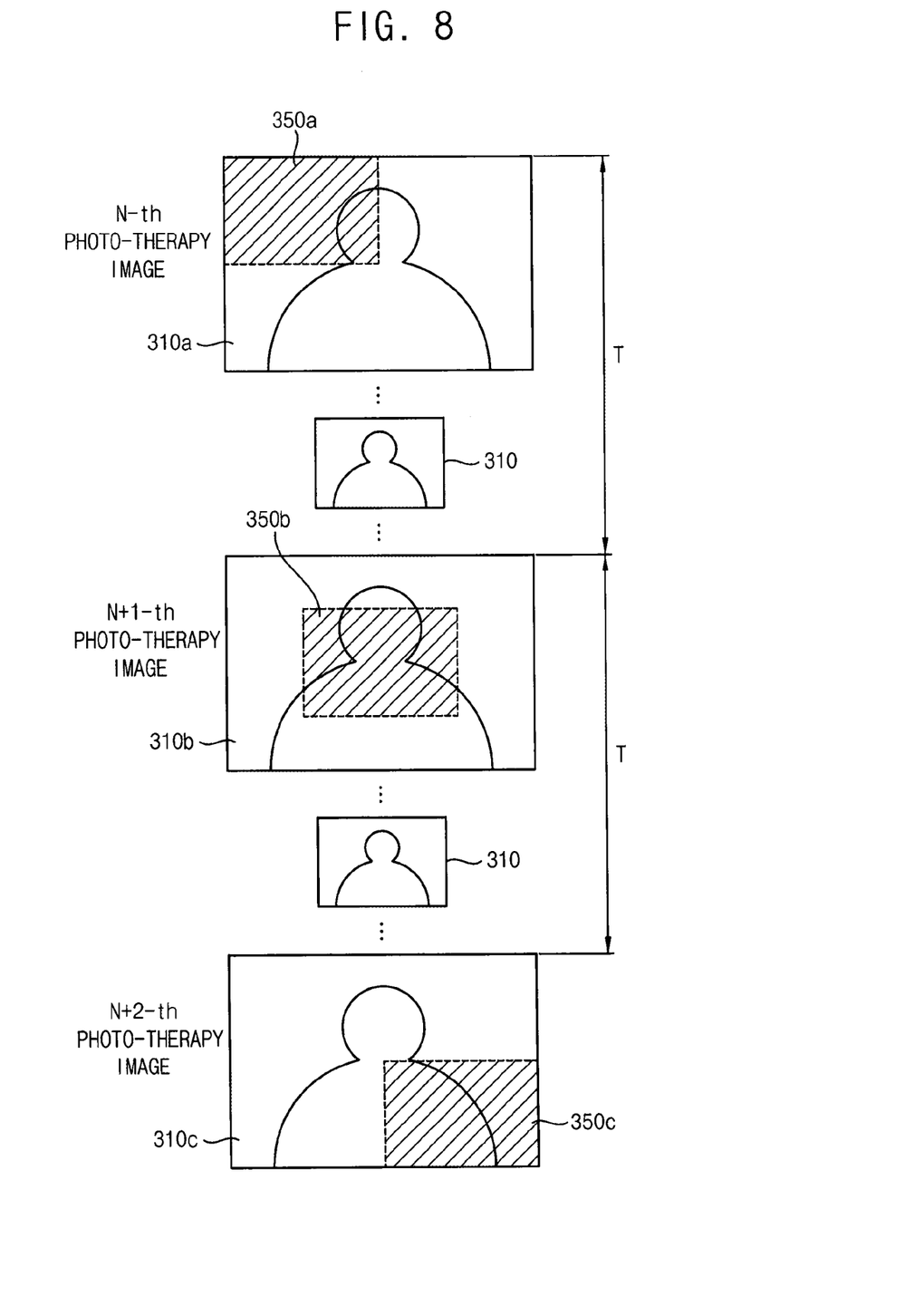
FIG. 8 is a diagram illustrating image frames displayed using the photo-therapy method of FIG. 7.

FIG. 7 is a flowchart illustrating a photo-therapy method using a display device in accordance with another further exemplary embodiment. FIG. 8 is a diagram illustrating image frames displayed using the photo-therapy method of FIG. 7.

Referring to FIG. 7, a display device first receives a viewing time input (representing an expected viewing time of a user) and a photo-therapy selection input (representing a photo-therapy selected by the user) (S500). The display device then calculates a period of a photo-therapy image based on the expected viewing time and a suggested treatment time of the selected photo-therapy (S520). In some embodiments, the display device may determine the period of the photo-therapy image such that the photo-therapy image is distributed uniformly (temporally) during the expected viewing time. In some embodiments, the display device may set the expected viewing time to be longer than a minimum viewing time, such that the number of frames per second of the photo-therapy image is less than the number of frames per second that is perceptible by the user. Accordingly, the user may undergo the photo-therapy without noticing (or perceiving) the photo-therapy image.

Next, the display device may display a synthesized image by synthesizing the photo-therapy image into a portion of a normal image with the calculated period (S540). For example, as illustrated in FIG. 8, the display device may display a normal image 310 for an original purpose of the display device, and may display a synthesized image by synthesizing photo-therapy images 350a, 350b and 350c into a portion of the normal images 310a, 310b and 310c with a period T. The period T is calculated based on the expected viewing time and the suggested treatment time. In some embodiments, a position of the portion of the normal images 310a, 310b and 310c, into which the photo-therapy images 350a, 350b and 350c are synthesized, may be randomly determined each time the synthesized image is displayed. For example, an N-th photo-therapy image 350a may be located at a top-left portion of a screen; an N+1-th photo-therapy image 350b may be located at a center portion of the screen; and an N+2-th photo-therapy image 350c may be located at a bottom-right portion of the screen. Since the positions of the photo-therapy images 350a, 350b and 350c are randomly changed, the photo-therapy images 350a, 350b and 350c may be imperceptible to the user.

As described above, the photo-therapy method using the display device according to the embodiment of FIGS. 7 and 8 allows the synthesized image to be displayed while displaying the normal image. The synthesized image is obtained by synthesizing the photo-therapy image into the portion of the normal image with the period (the period being calculated based on the expected viewing time and the suggested treatment time). Accordingly, the user may undergo the photo-therapy while watching the normal image. Furthermore, the exemplary display device may determine the period of the photo-therapy image to be longer than the period that is perceptible by the user. Accordingly, the user may undergo the photo-therapy without noticing (or perceiving) the photo-therapy image. Furthermore, because the position of the portion of the normal image (into which the photo-therapy image is synthesized) is randomly determined each time the synthesized image is displayed, the photo-therapy image may be further imperceptible to the user. In addition, in some embodiments, the exemplary photo-therapy method may allow various photo-therapies to be provided to a user using a single display device.

Figure 9:
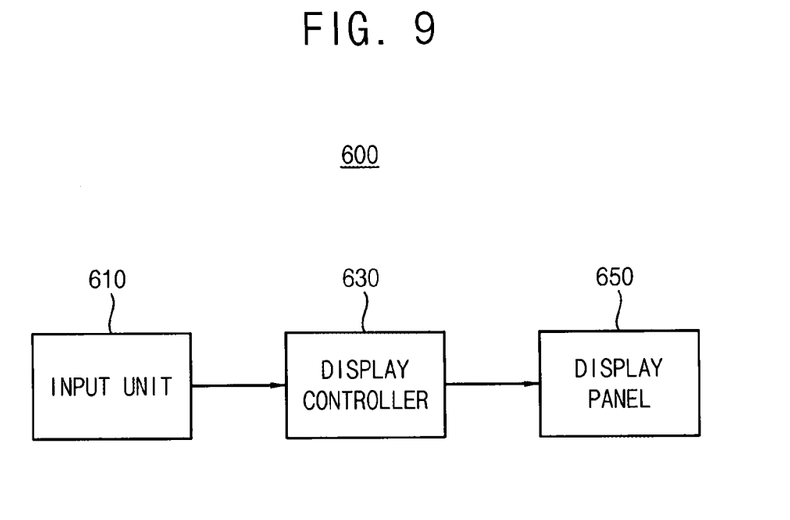
FIG. 9 is a block diagram illustrating a display device in accordance with an exemplary embodiment.

FIG. 9 is a block diagram illustrating a display device in accordance with an exemplary embodiment.

Referring to FIG. 9, a display device 600 includes a display panel 650, an input unit 610, and a display controller 630.

The display panel 650 may display a normal image for an original purpose of the display device 600. The display panel 650 may further display a photo-therapy image for a photo-therapy (such as anti-inflammatory therapy, pimple therapy, wrinkle therapy, skin lightening therapy, biorhythm control, depression therapy, etc.). The display panel 650 may include a liquid crystal display (LCD) panel, an organic light emitting diode (OLED) panel, a plasma display panel (PDP), a field emission display (FED) panel, a flexible display panel, etc.

The input unit 610 may receive a viewing time input (representing an expected viewing time of a user) and a photo-therapy selection input (representing a photo-therapy selected by the user). The input unit 610 may be implemented using input devices such as touchscreens, keypads, keyboards, mouse, etc.

The display controller 630 may receive the viewing time input and the photo-therapy selection input that are input to the input unit 610. The display controller 630 may then calculate a period of the photo-therapy image based on the expected viewing time (from the viewing time input) and a suggested treatment time of the selected photo-therapy (from the photo-therapy selection input). For example, the display controller 630 may calculate the period of the photo-therapy image such that the photo-therapy image is distributed uniformly (temporally) during the expected viewing time. The period of the photo-therapy image is proportional to the expected viewing time and inversely proportional to the suggested treatment time. Furthermore, in some embodiments, the display controller 630 may set the expected viewing time to be longer than a minimum viewing time, such that the period of the photo-therapy image is determined to be longer than a period that is perceptible by the user. Accordingly, the user may undergo the photo-therapy without noticing (or perceiving) the photo-therapy image.

Furthermore, the display controller 630 may control the display panel 650 to display the photo-therapy image with the calculated period while displaying the normal image. In some embodiments, the display controller 630 may control the display panel 650 to display a synthesized image by synthesizing the photo-therapy image and the normal image with the calculated period. In other embodiments, the display controller 630 may control the display panel 630 to display the photo-therapy image by inserting the photo-therapy image between the normal images with the calculated period. In some other embodiments, the display controller 630 may control the display panel 650 to display a synthesized image by synthesizing the photo-therapy image into a portion of the normal image with the calculated period.

The display controller 630 may include a processor that controls an operation of the display device 600. The processor may include a microprocessor, a central processing unit (CPU), etc. The display device 600 may further include a memory device for storing data required for the operation of the display device 600. For example, the memory device may include at least one non-volatile memory device such as an erasable programmable read-only memory (EPROM) device, an electrically erasable programmable read-only memory (EEPROM) device, a flash memory device, a phase change random access memory (PRAM) device, a resistance random access memory (RRAM) device, a nano floating gate memory (NFGM) device, a polymer random access memory (PoRAM) device, a magnetic random access memory (MRAM) device, a ferroelectric random access memory (FRAM) device, etc, and/or at least one volatile memory device such as a dynamic random access memory (DRAM) device, a static random access memory (SRAM) device, a mobile dynamic random access memory (mobile DRAM) device, etc. In some embodiments, the display device 600 may further include a storage device, such as a solid state drive (SSD) device, a hard disk drive (HDD) device, a CD-ROM device, etc. In some embodiments, the display device 600 may further include a power supply for supplying power for the operation of the display device 600.

The display device 600 may include any electronic device including the display panel 650, such as a digital television (TV), a 3D TV, a smart TV, a personal computer (PC), a home appliance, a laptop computer, a tablet computer, a cellular phone, a smart phone, a personal digital assistants (PDA), a portable multimedia player (PMP), a digital camera, a music player, a portable game console, a navigation device, etc.

It should be understood that the above-described embodiments are merely exemplary, and should not be construed as limiting the inventive concept. While the inventive concept has been described with reference to exemplary embodiments, it will be understood by those of ordinary skill in the art that various modifications may be made to the described embodiments without departing from the spirit and scope of the disclosure.

What is claimed is:

1. A photo-therapy method using a display device, the photo-therapy method comprising:
    providing a display device configured to display a normal image;
    receiving a viewing time input and a photo-therapy selection input, wherein the viewing time input represents an expected viewing time of a user and the photo-therapy selection input represents an expected viewing time of a user and the photo-therapy selection input represents a photo-therapy selected by the user;
    calculating a period of time for displaying a photo-therapy image based on the expected viewing time and a suggested treatment time of the selected photo-therapy;
    inserting the photo-therapy image into the normal image during the period of the photo-therapy image; and
    displaying image frames on the display device including the normal image interposed with the photo-therapy image,
    wherein the photo-therapy image includes at least a portion of color-amplified sub-pixels, and wherein an amplified color of the color-amplified sub-pixels is determined by the user's selection input for the photo-therapy.

2. The photo-therapy method of claim 1, wherein the photo-therapy image is distributed uniformly temporally during the expected viewing time.

3. The photo-therapy method of claim 1, wherein the period of the photo-therapy image is proportional to the expected viewing time, and is inversely proportional to the suggested treatment time.

4. The photo-therapy method of claim 1, wherein the period of the photo-therapy image is longer than a period that is perceptible by the user.

5. The photo-therapy method of claim 1, wherein the expected viewing time is longer than a minimum viewing time, such that a number of frames per second of the photo-therapy image is less than a number of frames per second that is perceptible by the user.

6. The photo-therapy method of claim 5, further comprising:
    informing the user that the expected viewing time is shorter than the minimum viewing time when a first viewing time input is received, wherein the first viewing time input indicates the expected viewing time is shorter than the minimum viewing time; and
    further receiving a second viewing time input from the user.

7. The photo-therapy method of claim 1, wherein displaying the photo-therapy image comprises:
    displaying a synthesized image by synthesizing the photo-therapy image and the normal image with the calculated period.

8. The photo-therapy method of claim 7, wherein the synthesized image is generated by adding a predetermined value to at least one sub-pixel data, wherein the at least one sub-pixel data is selected from among red sub-pixel data, green sub-pixel data, and blue sub-pixel data of the normal image based on the selected photo-therapy.

9. The photo-therapy method of claim 7, wherein the synthesized image is generated by multiplying a predetermined value with at least one sub-pixel data, wherein the at least one sub-pixel data is selected from among red sub-pixel data, green sub-pixel data, and blue sub-pixel data of the normal image based on the selected photo-therapy.

10. The photo-therapy method of claim 7, wherein the synthesized image is generated by converting at least one sub-pixel data to a maximum sub-pixel data, wherein the at least one sub-pixel data is selected from among red sub-pixel data, green sub-pixel data, and blue sub-pixel data of the normal image based on the selected photo-therapy.

11. The photo-therapy method of claim 1, wherein displaying the photo-therapy image comprises:
    displaying the photo-therapy image by inserting the photo-therapy image between normal images with the calculated period.

12. The photo-therapy method of claim 1, wherein displaying the photo-therapy image comprises:
    displaying a synthesized image by synthesizing the photo-therapy image into a portion of the normal image with the calculated period.

13. The photo-therapy method of claim 12, wherein a position of the portion of the normal image into which the photo-therapy image is synthesized is randomly determined each time the synthesized image is displayed.

14. The photo-therapy method of claim 1, wherein the photo-therapy is an anti-inflammatory therapy, a pimple therapy, or a wrinkle therapy, and wherein the amplified color is red.

15. The photo-therapy method of claim 1, wherein the photo-therapy is a skin lightening therapy, and the amplified color is green.

16. The photo-therapy method of claim 1, wherein the photo-therapy is a biorhythm control or depression therapy, and the amplified color is blue.

17. The photo-therapy method of claim 1, wherein the normal image is selected from a group comprising a television program, a video, and a game.

* * * * *